United States Patent [19]

Schach et al.

[11] Patent Number: 5,476,976
[45] Date of Patent: Dec. 19, 1995

[54] PROCESS FOR PREPARING FLUORONITROBENZENES

[75] Inventors: Thomas Schach, Gernsheim; Theodor Papenfuhs, Frankfurt am Main, both of Germany

[73] Assignee: Hoechst AG, Frankfurt, Germany

[21] Appl. No.: 277,475

[22] Filed: Jul. 19, 1994

[30] Foreign Application Priority Data

Jul. 21, 1993 [DE] Germany ............. 43 24 367.3

[51] Int. Cl.⁶ ........................................... C07C 201/2
[52] U.S. Cl. ............... 568/938; 570/127; 570/141; 570/170
[58] Field of Search .............. 568/938; 570/127, 570/141, 170

[56] References Cited

U.S. PATENT DOCUMENTS

| | | | |
|---|---|---|---|
| 3,064,058 | 11/1962 | Duesel et al. | 568/937 |
| 3,453,337 | 7/1969 | Bennett | 570/147 |
| 4,069,262 | 1/1978 | Kunz | 570/171 |
| 4,140,719 | 2/1979 | Tull et al. | 564/417 |
| 4,229,365 | 10/1980 | Oeser et al. | 568/938 X |
| 4,287,374 | 9/1981 | North | 568/937 |
| 4,418,229 | 11/1983 | White | 568/938 X |
| 4,684,734 | 8/1987 | Kaieda et al. | 546/345 |
| 4,937,397 | 6/1990 | Pews et al. | 570/147 |
| 5,081,288 | 1/1992 | Blank et al. | 570/147 X |
| 5,294,742 | 3/1994 | Schach et al. | 568/938 |
| 5,315,043 | 5/1994 | Fernandez et al. | 568/932 |
| 5,349,098 | 9/1994 | Kumai et al. | 570/141 |

FOREIGN PATENT DOCUMENTS

WO87/04149 7/1987 WIPO.

Primary Examiner—Gary L. Geist
Assistant Examiner—Valerie Fee
Attorney, Agent, or Firm—Connolly and Hutz

[57] ABSTRACT

Fluoronitrobenzenes are prepared in an advantageous way from the corresponding chloronitrobenzenes and an alkali metal fluoride by means of a chlorine-fluorine exchange reaction with replacement of a chlorine atom by a fluorine atom, by catalyzing the reaction with a quaternaryammonium compound which comprises at least one alkoxypolyoxyalkyl radical.

15 Claims, No Drawings

PROCESS FOR PREPARING FLUORONITROBENZENES

The present invention relates to an improved process for preparing fluoronitrobenzenes with replacement of a chlorine atom by a fluorine atom by reaction of the corresponding chloronitrobenzenes with alkali metal fluorides in the presence of a novel catalyst system. The halogen exchange, preferably that of activated chloronitrobenzenes, is a customary method of introducing fluoro substituents into an aromatic system. In general, the reaction is carried out in the presence of aprotic dipolar solvents and alkali metal fluorides as fluoride source (U.S. Pat. No. 3,064,058). Prominent disadvantages of these processes are high reaction temperatures, moderate product yields and long reaction times.

As alternatives, use can be made of conventional phase transfer catalysts which enable some of the above-described disadvantages to be improved. Other problems, such as, for example, poor stirrability of the reaction suspension in solvent-free processes, remain. The phase transfer catalysts hitherto used have been quaternary alkylammonium alkylphosphonium salts (U.S. Pat. No. 4,287,374), pyridinium salts (WO 87/04149) or crown ethers, some of which show only low reactivities or are only moderately stable at the reaction temperatures required.

In view of these limitations and disadvantages, there was a great need for an improved process by means of which the disadvantages inherent in the known processes are avoided and good to very good yields, relatively low reaction temperatures and shortened reaction times are made possible and relatively small amounts of polymeric decomposition products are obtained. Particular importance has been attached to, in particular, coping with stirring problems and workup problems in solvent-free processes and in processes using only very small amounts of solvent.

It has been found that fluoronitrobenzenes and chlorofluoronitrobenzenes can be prepared in an advantageous manner by reacting the corresponding chloronitrobenzenes with alkali metal fluorides in the presence of a quaternary ammonium compound comprising at least one alkoxypolyoxyalkyl radical.

The present invention provides a process for preparing fluoronitrobenzenes of the formula (5)

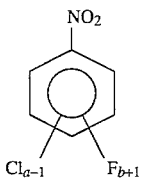

by reaction of a compound of the formula (4)

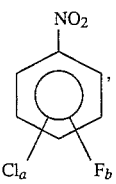

in which a is the number 1 or 2 and b is a number from 0 to 2, with an alkali metal fluoride in the presence of a catalyst, wherein the catalyst consists essentially of a) one or more quaternary ammonium compound(s) of the formula (1)

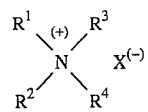

in which $R^1$, $R^2$ and $R^3$ are identical or different and are a linear or branched alkoxypolyoxyalkyl radical of the formula $-(C_mH_{2m}O)_pR^5$, in which $R^5$ is hydrogen or a linear or branched alkyl radical having from 1 to 16, preferably from 1 to 8, carbon atoms, m is an integer from 1 to 10, preferably from 1 to 5, and p is a number from 1 to 15, preferably from 2 to 10; or a linear or branched alkyl radical having from 1 to 30, preferably from 1 to 18, carbon atoms; or an unsubstituted phenyl or naphthyl radicals or a substituted phenyl or naphthyl radical, with the substituents being halogen, $C_1$–$C_4$-alkyl, $C_1$–$C_4$alkoxy, nitro or cyano;

$R^4$ is a linear or branched alkoxypolyoxyalkyl radical of the formula $-(C_mH_{2m}O)_pR^5$; and $X^{\ominus}$ is an inorganic anion, preferably fluoride, chloride, bromide, $SO_4^{2-}/2$ or hydrogen sulfate;

or of a mixture of the component a) and b) one or more quaternary ammonium salt(s) or phosphonium salt(s) of the formula (2)

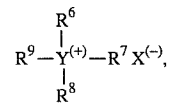

in which $R^6$, $R^7$, $R^8$ and $R^9$ are identical or different and are a linear or branched alkyl radical having from 1 to 22, preferably from 1 to 16, carbon atoms; or an unsubstituted or substituted aryl radical or a $C_1$–$C_4$-alkyl-aryl radical, with aryl being phenyl or naphthyl and said substituents being halogen, $C_1$–$C_4$alkyl, $C_1$–$C_4$-alkoxy, nitro or cyano; and Y is N or P;

or of a mixture of the component a) and c) one or more polyether(s) of the formula (3)

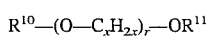

in which $R^{10}$ and $R^{11}$ are identical or different and are hydrogen or a linear or branched alkyl radical having from 1 to 16, preferably from 1 to 8, carbon atoms, x is an integer from 2 to 6, preferably 2 or 3, and r is a number from 0 to 20, preferably from 4 to 14;

or a crown ether;

or of a mixture of the components a), b) and c).

By means of the process of the invention, a chlorine atom in the starting compound of the formula (4) is replaced by a fluorine atom.

The catalyst preferably consists exclusively of component a), but it can be advantageous to use a mixture of the components a) and b) or of the components a) and c) or of the components a), b) and c).

The mixing ratios of the components a) and b), a) and c) and also a), b) and c) can vary within a wide range, with the proviso that the component a) makes up at least 5% by weight, preferably from 20 to 80% by weight, of the total catalyst.

In the linear or branched alkoxypolyoxyalkyl radical of the formula —$(C_mH_{2m}O)_pR^5$ present in the compound of the formula (1), identical or different alkoxy units can be linked to one another. The number of the linear or branched alkoxypolyoxyalkyl radicals present in the compound of the formula (1) is preferably 1 or 2. For the purposes of the present invention, particularly preferred compounds of the formula (1) are dimethyldi (ethoxypolyoxypropyl) ammonium chloride, dimethyldi (ethoxypolyoxypropyl methyl ether) ammonium chloride, dimethyl (ethoxypolyoxypropyl) (ethoxypolyoxypropyl methyl ether) ammonium chloride, dimethyldi (ethoxypolyoxyethyl) ammonium chloride, dimethyldi(ethoxypolyoxyethyl methyl ether) ammonium chloride, dimethyl (ethoxypolyoxyethyl) (ethoxypolyoxyethyl methyl ether)ammonium chloride, each having a mean chain length p of 3, furthermore trimethyl ethoxypolyoxypropyl) ammonium chloride and trimethyl (ethoxypolyoxypropyl methyl ether) ammonium chloride, each having a mean chain length p of 8, or a mixture of the specified compounds.

The described compounds of the formula (1) can be prepared in a known manner (U.S. Pat. No. 3,123,6411 U.S. Pat. No. 3,141,905) from the corresponding ethanolamines which, after reaction with alkylene oxides and subsequent quaternization with or without simultaneous etherification, give the desired compounds in good yields.

For the purposes of the present invention, preferred compounds of the formula (2) are octadecyltrimethylammonium chloride, distearyldimethylammonium chloride, tetramethylammonium chloride, tetramethylammonium bromide, hexadecyltrimethylammoniumchloride, benzyltrimethylammonium chloride, hexadecyltributylphosphonium bromide, stearyltributylphosphoniumbromide, tetrabutylphosphonium chloride, tetrabutylphosphonium bromide and tetraoctylphosphoniumbromide.

For the purposes of the present invention, preferred polyethers of the formula (3) possess a mean molecular mass between 300 and 800. Particular preference is given to a mixture of polyethylene glycol dimethyl ethers having chain lengths r of from 6 to 17 and a mean molecular mass of 500.

In place of or in combination with polyethers of the formula (3), customary crown ethers, for example 18-crown-6, can also be used.

Suitable starting compounds of the formula (4) for the process of the invention are: monochloronitrobenzenes such as, for example, 2-chloronitrobenzene and 4-chloronitrobenzene; dichloronitrobenzenes such as, for example, 2,3-dichloronitrobenzene, 3,4-dichloronitrobenzene, 2,5-dichloronitrobenzene, 4-chloro-3-fluoronitrobenzene and 2-chloro-5-fluoronitrobenzene.

End products of the formula (5) are, for example: monofluoronitrobenzenes such as, for example, 2-fluoronitrobenzene and 4-fluoronitrobenzene; chlorofluoronitrobenzenes such as, for example, 3-chloro-2-fluoronitrobenzene, 3-chloro-4-fluoronitrobenzene and 5-chloro-2-fluoronitrobenzene; difluoronitrobenzenes such as, for example, 3,4-difluoronitrobenzene and 2,5-difluoronitrobenzene.

The alkali metal fluorides used are preferably potassium fluoride, rubidium fluoride or cesium fluoride or combinations of these, in particular potassium fluoride. It is an advantage of the process of the invention that use can be made of alkali metal fluorides whose water content can be up to 3%. This makes it possible, for example, to use technical grade potassium fluoride without pretreatment.

In the process of the invention, the catalyst is advantageously used in amounts of from 1 to 35% by weight, preferably from 2 to 20% by weight, based on the aromatic starting compound. The molar ratio of catalyst to starting compound is here equal to or less than 1:8, preferably from 1:15 to 1:100.

As regards the molar ratio of the alkali metal fluoride to the starting compound, from 60 to 200 mol %, preferably from 100 to 140 mol %, based on each chlorine atom to be replaced, of alkali metal fluoride are used. While temperatures of from 200° C. to over 300° C. have hitherto been required for chlorine-fluorine exchange reactions, the reaction temperatures of the process of the invention are from 80° to 220° C., preferably from 90° to 180° C, in particular from 120° to 170° C.

The process of the invention can be carried out in the presence or absence of solvents. If solvents are used, suitable solvents are aprotic and dipolar aprotic and also protic solvents. Suitable dipolar aprotic solvents are, for example, dimethyl sulfoxide, dimethyl sulfone, sulfolane, dimethylformamide, dimethylacetamide, 1,3-dimethylimidazolin-2-one, acetonitrile and benzonitrile. Suitable aprotic solvents without pronounced dipolar character are, for example, benzene, toluene, xylene, chlorotoluenes, chlorobenzene and dichlorobenzenes. The use of protic solvents such as, for example, alcohols is likewise possible. The protic solvents used are methanol, ethanol, propanol, butanol, 1-propanol or polyalkylene glycols having ethylene, propylene or butylene units.

The aprotic or dipolar aprotic solvent can be used in any amounts, however preference is given to small amounts in the range from 5 to 30% by weight, based on the aromatics used. When using protic solvents, the amounts used are in the range from 0.1 to 5% by weight, preferably from 0.1 to 2% by weight, based on the aromatic used.

The catalyst of the invention can be used at atmospheric pressure and also at superatmospheric or subatmospheric pressure. These properties are utilized, for example, by adding small amounts of a low-boiling aprotic solvent which forms an azeotrope with water, such as, for example, benzene, xylene, mesitylene or toluene, to the reaction suspension prior to the start of the reaction. Subsequently, a part of the solvent is, by application of a vacuum, again removed together with water from the reaction suspension. This process procedure allows the reaction rate and the yield to be increased and the formation of byproducts to be minimized.

The process of the invention can be carried out in the presence or absence of atmospheric oxygen; working under protective gases such as, for example, argon or nitrogen is preferred. In the process of the invention, it must be ensured that the reaction mixture is well mixed during the whole reaction.

Fluoronitrobenzenes are important as intermediates in the field of crop protection and as synthetic building blocks for pharmaceuticals and dyes.

The following examples illustrate the process of the invention, without limiting it to them. For the purposes of the present invention, "polyethylene glycol dimethyl ether 500" is the said polyether having a mean molecular mass of about 500. The trimethyl (ethoxypolyoxypropyl)ammonium chloride used in the examples has a mean chain length p of 8 and was used as product having a purity of from 84 to 89% by weight. This product additionally contains from 10 to 13% by weight of free polypropylene glycol and up to 2% by weight of water.

The dimethyldi(ethoxypolyoxypropyl)ammonium chloride used has a mean chain length p of 3 and is a product having a purity of from 90 to 95% by weight which additionally contains from 5 to 10% by weight of polypropylene glycol and about 0.2% of water.

If the two catalysts were used as etherified compounds, the polypropylene glycols were likewise in etherified form. In the case of dimethoxydi(ethoxypolyoxypropyl methyl ether) ammonium chloride, the degree of etherification was 86%.

The course of the reaction over time was followed by means of gas chromatographic analysis (GC) and the amount of the desired product present in the reaction mixture in each case was given in the form of GC percentage areas.

EXAMPLE 1

3-Chloro-2-fluoronitrobenzene

In a 2.5 liter flange flask fitted with a distillation bridge and impeller stirrer, 150 g (2.58 mol) of potassium fluoride, 37.5 g (0.05 mol) of trimethyl(ethoxypolyoxypropyl)ammonium chloride and 9.9 g (0.09 mol) of tetramethylammonium chloride were introduced at 120° C. into the melt of 620 g (3.23 mol) of 2,3-dichloronitrobenzene. Subsequently, 20 g (0.19 mol) of xylene were added and the reaction suspension was azeotropically dried by application of a vacuum of 40 mbar and heating to 150° C. After the xylene had been distilled off, the reaction bridge was replaced by a reflux condenser and the reaction suspension was heated to 150° C. and stirred for 21 hours at this temperature.

Subsequently, the reaction suspension was cooled to 70° C. and filtered with suction (70° C.). The salts separated off were washed twice with a total of 180 g of xylene and the combined organic phases were fractionated. 324 g (72% of theory) of 3-chloro-2-fluoronitrobenzene were isolated. Amounts of 3-chloro-2-fluoronitrobenzene formed, according to GC analysis:

after 6 hours: 41 GC area-%
after 21 hours: 82 GC area-%.

Comparative Example 1

3-Chloro-2-fluoronitrobenzene a) In a 1-liter flange flask fitted with a distillation bridge and stirrer, 139 g (2.4 mol) of potassium fluoride were introduced at 120° C. into the melt of 576 g (3.0 mol) of 2,3-dichloronitrobenzene. Subsequently, 20 g (0.19 mol) of xylene were added and the reaction suspension was azeotropically dried by application of a vacuum of 60 mbar and heating to 150° C. After the xylene had been distilled off, the distillation bridge was replaced by a reflux condenser, the reaction suspension was heated to 190° C. and stirred for 6 hours at this temperature. Amount of 3-chloro-2-fluoronitrobenzene formed: 0.5 GC area-% after 6 hours.

b) In a 1-liter flange flask fitted with a distillation bridge and stirrer, 29 g (0.06 mol) of polyethylene glycol dimethyl ether 500 and 139 g (2.4 mol) of potassium fluoride were introduced at 120° C. into the melt of 576 g (3.0 mol) of 2,3-dichloronitrobenzene. Subsequently, 20 g (0.19 mol) of xylene were added and the reaction suspension was azeotropically dried by application of a vacuum of 60 mbar and heating to 150° C. After the xylene had been distilled off, the distillation bridge was replaced by a reflux condenser, the reaction suspension was heated to 190° C. and stirred for 6 hours at this temperature. Amount of 3-chloro-2-fluoronitrobenzene formed: 11 GC area-% after 6 hours.

EXAMPLE 2

2-Fluoronitrobenzene

In a 2-liter flange flask fitted with a distillation bridge and impeller stirrer, 348.6 g (6.0 mol) of potassium fluoride, 71.1 g (0.1 mol) of trimethyl (ethoxypolyoxypropyl)ammonium chloride and 23.5 g (0.21 mol) of tetramethylammonium chloride were introduced at 120° C. into the melt of 939 g (6.0 mol) of 2-chloronitrobenzene. Subsequently, 100 g (0.38 mol) of xylene were added and the reaction suspension was heated to 150° C., the xylene was removed under reduced pressure and the mixture was stirred for 21 hours at this temperature. Subsequently, the reaction suspension was cooled to 70° C. and filtered with suction. The salts separated off were washed twice with a total of 360 g of xylene and the combined organic phases were fractionated. 356 g (63% of theory) of 2-fluoronitrobenzene were isolated. Amount of 2-fluoronitrobenzene formed, according to GC analysis:

After 6 hours: 39 GC area-%
After 21 hours: 64 GC area-%.

EXAMPLE 3

2-Fluoronitrobenzene

In a 2-liter flange flask fitted with a distillation bridge and impeller stirrer, 290.5 g (5.0 mol) of potassium fluoride, 71.1 g (0.1 mol) of trimethyl(ethoxypolyoxypropyl)ammonium chloride and 17.0 g (0.16 mol) of tetramethylammonium chloride were introduced at 120° C. into the melt of 630 g (4.0 mol) of 2-chloronitrobenzene. Subsequently, 100 g (0.38 mol) of xylene were added and the reaction suspension was heated to 150° C., the xylene was removed under reduced pressure and the mixture was stirred for 21 hours at this temperature. Subsequently, the reaction suspension was cooled to 70° C. and filtered with suction. The salts separated off were washed twice with a total of 360 g of xylene and the combined organic 35 phases were fractionated. 417 g (74% of theory) of 2-fluoronitrobenzene were isolated. Amount of 2-fluoronitrobenzene formed, according to GC analysis:

After 6 hours: 37 GC area-%
After 21 hours: 74 GC area-%.

EXAMPLE 4

2-Fluoronitrobenzene

In a 2-liter flange flask fitted with a distillation bridge and impeller stirrer, 290.5 g (5.0 mol) of potassium fluoride, 71.1 g (0.1 mol) of trimethyl (ethoxypolyoxypropyl) ammonium chloride, 11.0 g (0.1 mol) of tetramethylammonium chloride and 17.7 g (0.035 mol) of polyethylene glycol dimethyl ether 500 were introduced at 120° C. into the melt of 630 g (4.0 mol) of 2-chloronitrobenzene. Subsequently, 100 g (0.38 mol) of xylene were added and the reaction mixture was stirred for 21 hours at a temperature of 150° C. Amount of 2-fluoronitrobenzene formed, according to GC analysis:

After 6 hours: 36 GC area-%
After 21 hours: 74 GC area-%.

Comparative Example 2

2-Fluoronitrobenzene

In a 2-liter flange flask fitted with a distillation bridge and impeller stirrer, 278.4 g (4.8 mol) of potassium fluoride and 23.5 g (0.21 mol) of tetramethylammonium chloride were introduced at 120° C. into the melt of 939 g (6.0 mol) of 2-chloronitrobenzene. Subsequently, 4 g (0.38 mol) of xylene were added and the reaction suspension was heated to 180° C., the xylene was removed under reduced pressure and the mixture was stirred for 21 hours at this temperature. Amount of 2-fluoronitrobenzene formed, according to GC analysis:

After 5 hours: 28.7 GC area-%
After 21 hours: 48.8 GC area-%.

EXAMPLE 5

3-Chloro-4-fluoronitrobenzene

In a 1-liter flange flask fitted with a distillation bridge and impeller stirrer, 240 g (4.1 mol) of potassium fluoride, 30 g (0.05 mol) of dimethyldi (ethoxypolyoxypropyl methyl ether)ammonium chloride and 30 g of xylene were introduced at 70° C. into the melt of 767 g (4.0 mol) of 3,4-dichloronitrobenzene, and the reaction suspension was azeotropically dried under reduced pressure up to 120° C. 498 g (2.84 mol) of 3-chloro-4-fluoronitrobenzene were isolated. Amount of 3-chloro-4-fluoronitrobenzene formed, according to GC analysis:

After 5 hours: 33 GC area-%
After 24 hours: 71 GC area-%.

We claim:
1. A process for preparing fluoronitrobenzenes of the formula

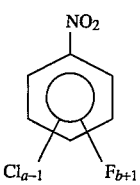
(5)

by reaction of a compound of the formula (4)

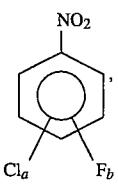
(4)

in which
the number 1 or 2 and
b is a number from 0 to 2,
with an alkali metal fluoride in the presence of a catalyst, wherein the catalyst consists essentially of
a) one or more quaternary ammonium compound(s) of the formula (1)

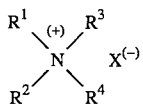
(1)

in which
$R^1$, $R^2$ and $R^3$ are identical or different and an a linear or branched alkoxypolyoxyalkyl radical of the formula $-(C_mH_{2m}O)_pR^5$, where in which $R^5$ is hydrogen or a linear or branched alkyl radical having from 1 to 16 carbon atoms, m is an integer from 1 to 10 and p is a number from 1 to 15;
or
a linear or branched alkyl radical having from 1 to 30 carbon atoms; or an unsubstituted phenyl or naphthyl radical; or a substituted phenyl or naphthyl radical, with the substituents being halogen, $C_1$-$C_4$-alkyl, $C_1$-$C_4$-alkoxy, nitro or cyano;

$R^4$ is a linear or branched alkoxypolyoxyalkyl radical of the formula $-(C_mH_{2m}O)_pR^5$;
where m, p and $R^5$ have the same meaning as above, and
$X^\ominus$ is an inorganic action;
or of a mixture of the component a) and b)
wherein
b) is one or more quaternary ammonium salt(s) or phosphonium salt(s) of the formula (2)

in which
$R^6$, $R^7$, $R^8$ and $R^9$ are identical or different and are a linear or branched alkyl radical having from 1 to 22 carbon atoms; or an unsubstituted or substituted aryl radical or a $C_1$-$C_4$-alkyl-aryl radical, with aryl being phenyl or naphthyl and said substitutents being halogen, $C_1$-$C_4$-alkyl, $C_1$-$C_4$-alkoxy, nitro or cyano; and
Y is N or P;
or of a mixture of the component a) and c)
wherein
c) is a crown ether or one or more polyether(s) of the formula (3) or a mixture thereof, $$R^{10}-(O-C_xH_{2x})_r-OR^{11} \qquad (3),$$

in which
$R^{10}$ and $R^{11}$ are identical or different and are hydrogen or a linear or branched alkyl radical having from 1 to 16 carbon atoms,
x is an integer from 2 to 6 and
r is a number from 0 to 20;
or of a mixture of the components a), b) and c).
2. The process as claimed in claim 1, wherein the catalyst consisting essentially of
a) one or more quaternary ammonium compound(s) of the formula (1)

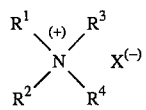
(1)

in which
$R^1$, $R^2$ and $R^3$ are identical or different and are a linear or branched alkoxypolyoxyalkyl radical of the formula $-(C_mH_{2m}O)_pR^5$, in which $R^5$ is hydrogen or a linear or branched alkyl radical having from 1 to 8 carbon atoms, m is an integer from 1 to 5 and p is a number from 2 to 10;
or
a linear or branched alkyl radical having from 1 to 18 carbon atoms; or an unsubstituted phenyl or naphthyl radical; or a substituted phenyl or naphthyl radical, with the substituents being halogen, $C_1$-$C_4$-alkyl, $C_1$-$C_4$-alkoxy, nitro or cyano;
$R^4$ is a linear or branched alkoxypolyoxyalkyl radical of the formula $-(C_mH_{2m}O)_pR^5$; wherein m, p and $R^5$ have the same meaning as above and
$X^\ominus$ is fluoride, chloride, bromide, $SO_4^{2-}/2$ or hydrogen sulfate;
or of a mixture of the component a) and b)
wherein b) is one or more quaternary ammonium salt(s) or phosphonium salt(s) of the formula (2)

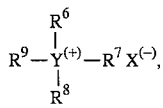
(2)

in which

R⁶, R⁷, R⁸ and R⁹ are identical or different and are a linear or branched alkyl radical having from 1 to 16 carbon atoms; or an unsubstituted or substituted aryl radical or a $C_1$–$C_4$-alkylaryl radical, with aryl being phenyl or naphthyl and said substituents being halogen, $C_1$–$C_4$-alkyl, $C_1$–$C_4$-alkoxy, nitro or cyano; and Y is N or P;

or of a mixture of the component a) and c)

wherein c) is a crown ether or one or more polyether(s) of the formula (3) or mixture thereof,

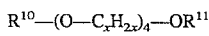
(3), in which $R^{10}$ and $R^{11}$ are identical or different and are hydrogen or a linear or branched alkyl radical having from 1 to 8 carbon atoms, x is the number 2 or 3 and r is a number from 4 to 14;

or of a mixture of the components a), b) and c).

3. The process as claimed in claim 1 wherein the component a) makes up at least 5% by weight, of the total catalyst.

4. The process as claimed in claim 1 wherein one or two alkoxypolyoxyalkyl radicals are present in the compound of the formula (1).

5. The process as claimed in claim 3 wherein the component a) is from 20 to 80% by weight of the total catalyst.

6. The process as claimed in claim 1 wherein the alkali metal fluoride is potassium fluoride, rubidium fluoride, cesium fluoride or a combination of these fluorides.

7. The process as claimed in claim 6 wherein the alkali metal fluoride is potassium fluoride.

8. The process as claimed in claim 1 wherein the molar ratio of catalyst to the compound of the formula (4) is equal to or less than 1:8.

9. The process as claimed in claim 8 wherein the molar ratio of catalyst to compound of the formula (4) is from 1:15 to 1:100.

10. The process as claimed in claim 1 wherein the reaction is carried out in the absence of a solvent.

11. The process as claimed in claim 1 wherein the reaction temperature is from 80° to 220° C.

12. The process as claimed in claim 11 wherein the reaction temperature is from 90° to 180° C.

13. The process as claimed in claim 1 wherein the reaction temperature is from 120° to 170° C.

14. The process as claimed in claim 1 wherein the compound of the formula (4) is 2-chloronitrobenzene, 4-chloronitrobenzene, 2,3-dichloronitrobenzene, 3,4-dichloronitrobenzene, 2,5-dichloronitrobenzene, 4-chloro-3-fluoronitrobenzene or 2-chloro-5-fluoronitrobenzene.

15. A process for preparing fluoronitrobenzenes of the formula (5)

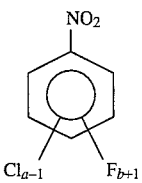
(5)

comprising reacting a compound of the formula (4)

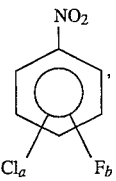
(4)

in which a is the number 1 or 2 and b is a number from 0 to 2, with an alkali metal fluoride in the presence of a catalyst, wherein said catalyst consists essentially of 1) component a), 2) components a) and b), 3) components a) and c) or 4) components a), b) and c)

wherein said components a), b) and c) are the following:

a) one or more quaternary ammonium compound(s) of the formula (1)

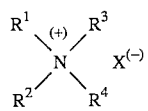
(1)

in which $R^1$, $R^2$ and $R^3$ are identical or different and are a linear or branched alkoxypolyoxyalkyl radical of the formula —$(C_mH_{2m}O)_pR^5$, in which $R^5$ is hydrogen or a linear or branched alkyl radical having from 1 to 16 carbon atoms, m is an integer from 1 to 10 and p is a number from 1 to 15; or a linear or branched alkyl radical having from 1 to 30 carbon atoms; or an unsubstituted phenyl or naphthyl radical; or a substituted phenyl or naphthyl radical, with the substituents being halogen, $C_1$–$C_4$-alkyl, $C_1$–$C_4$-alkoxy, nitro or cyano;

is a linear or branched alkoxypolyoxyalkyl radical of the formula —$(C_mH_{2m}O)_pR^5$; wherein m, p and $R^5$ have the same meaning as above and $X^{\ominus}$ is an inorganic action;

b) one or more quaternary ammonium salt(s) or phosphonium salt(s) of the formula (2)

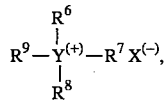 (2)

in which

R$^6$, R$^7$, R$^8$ and R$^9$ are identical or different and are a linear or branched alkyl radical having from 1 to 22 carbon atoms; or an unsubstituted or substituted aryl radical or a C$_1$–C$_4$-alkyl-aryl radical, with aryl being phenyl or naphthyl and said substituents being halogen, C$_1$–C$_4$-alkyl, C$_1$–C$_4$-alkoxy, nitro or cyano; and Y is N or P;

c) a crown ether or one or more polyether(s) of the formula (3)

$$R^{10}-(O-C_xH_{2x})_r-OR^{11} \qquad (3)$$

in which

R$^{10}$ and R$^{11}$ are identical or different and are hydrogen or a linear or branched alkyl radical having from 1 to 16 carbon atoms, x is an integer from 2 to 6 and r is a number from 0 to 20.

* * * * *

UNITED STATES PATENT AND TRADEMARK OFFICE
CERTIFICATE OF CORRECTION

PATENT NO. : 5,476,976  
DATED : Dec. 19, 1995  
INVENTOR(S) : Schach et al

Page 1 of 2

It is certified that error appears in the above-indentified patent and that said Letters Patent is hereby corrected as shown below:

In claim 1, in column 7, line 44, the phrase "the number" should read --a is the number--.

In claim 1, in column 7, line 57, the phrase "and an a linear" should read --and are a linear--.

In claim 1, in column 8, line 4, the phrase "inorganic action" should read --inorganic anion--.

In claim 15, in column 10, line 63, the phrase "is a linear" should read --$R^4$ is a linear--.

UNITED STATES PATENT AND TRADEMARK OFFICE
CERTIFICATE OF CORRECTION

PATENT NO. : 5,476,976

DATED : Dec. 19, 1995

INVENTOR(S) : Schach et al

It is certified that error appears in the above-indentified patent and that said Letters Patent is hereby corrected as shown below:

In claim 15, in column 10, line 66, the phrase "inorganic action" should read -- inorganic anion--.

Signed and Sealed this

Third Day of December, 1996

BRUCE LEHMAN

Attest:

Attesting Officer

Commissioner of Patents and Trademarks